United States Patent [19]
Deline et al.

[11] Patent Number: 6,127,536
[45] Date of Patent: Oct. 3, 2000

[54] SYNTHESIS OF A TETRAAMIDO MACROCYCLE LIGAND

[75] Inventors: James E. Deline, Livermore; Michael M. Ott, Oakland; Kevin A. Klotter, Livermore, all of Calif.

[73] Assignee: The Clorox Company, Oakland, Calif.

[21] Appl. No.: 09/318,410

[22] Filed: May 25, 1999

[51] Int. Cl.[7] .................................................. C07D 225/00
[52] U.S. Cl. ........................ 540/460; 540/461; 540/452; 540/465
[58] Field of Search .................................... 540/455, 460, 540/461, 465

[56] References Cited

U.S. PATENT DOCUMENTS 5,853,428  12/1998  Collins et al. .............................. 8/107

OTHER PUBLICATIONS

Bradshaw et al., Chap VIII in Aza–Crown Macrocycles., John Wiley & Sons 1993, p. 402.

Primary Examiner—Mukund J. Shah
Assistant Examiner—Pavanaram K Sripada
Attorney, Agent, or Firm—Mark E. Baze; Joel J. Hayashida

[57] ABSTRACT

An improved synthesis for preparing a tetraamido-macrocyclic ligand, such as 5,6-Benzo-3,8,11,13-tetraoxo-2,2,9,9-tetramethyl-12,12-diethyl-1,4,7,10-tetraazacyclotridecane, $H_4$, in greatly improved yield and in a commercially viable manner, comprising the steps of dissolving a quantity of a 1,2-bis(2-aminoalkanamido) benzene in a solution comprised of ethyl acetate and methylene chloride to yield a first reaction solution; dissolving a quantity of a malonyl dihalide in an ethyl acetate solution to yield a second reaction solution; adding the first reaction solution and the second reaction solution to a reaction vessel containing a third reaction solution comprised of refluxing ethyl acetate solution and an acid scavenger to form a reaction mixture; and isolating a solid product comprised of the tetraamido-macrocycle directly from the reaction mixture by filtration.

20 Claims, 1 Drawing Sheet

SYNTHESIS OF A TETRAAMIDO MACROCYCLE LIGAND

FIELD OF THE INVENTION

The present invention relates to tetraamido macrocyclic ligands that form complexes with transition metals, and more particularly to an improved synthesis of such macrocycles as exemplified by 5,6-Benzo-3,8,11,13-tetraoxo-2,2,9,9-tetramethyl-12,12-diethyl-1,4,7,10-tetraazacyclotridecane, $H_4$.

BACKGROUND OF THE INVENTION

The use of transition metal chelates as catalysts for bleaching agents is well known in the art. For example, U.S. Pat. No. 4,119,557, issued to Postlethwaite, discloses the use of iron-polycarboxyamine complexes with hydrogen peroxide releasing substances to clean fabrics. Similarly, U.S. Pat. No. 5,244,594 (Favre et al.), U.S. Pat. No. 5,246,621 (Favre et al.), U.S. Pat. No. 5,194,416 (Jureller et al.), and U.S. Pat. No. 5,314,635 (Hage et al.) describe the use of manganese complexes of nitrogen- (or other heteroatom-) coordinated macrocycles as catalysts for peroxy compounds.

The utility of compounds of this type has motivated researchers to develop new ligands that both stabilize the catalyst complex and that are able to withstand an oxidative environment. Promising ligands in this respect are the tetraamido macrocycles represented by structure 10 shown in FIG. 1 which, when complexed with a transition metal such as iron, afford particularly good dye transfer inhibition capabilities.

An azide-based, four-step synthesis of the macrocycle is described by Collins et al. in *J. Am. Chem. Soc.*, vol. 113, No. 22, page 8419 (1991). A problem with this synthesis is that it produces the tetraamido macrocycle in yields of only about 12% (starting from 1,2-phenylenediamine, as shown in the scheme at page 8422 of the article) and employs isolation techniques which cannot be adapted to large scale production. An alternative synthesis described in U.S. Pat. No. 5,853,428, issued also to Collins, employs a ring forming strategy that is the reverse of the earlier published synthesis. This later synthesis, described by Collins as now being his preferred synthesis, and in what is clearly an effort to overcome the shortcomings of the prior synthetic method, provides the macrocycle structure in two steps and in an improved overall yield of about 18% (starting from diethyl malonyl dichloride, as shown in the general scheme at col. 15 of the patent). However, the first step, a double coupling, is said to require 72–144 hours for completion, while the second step, a ring closure, requires 48–110 hours. Further, the use of large amounts of anhydrous pyridine as solvent are apparently required in both steps, which is commercially prohibitive. For commercial purposes, a much more efficient synthesis of the tetraamido macrocycle is required than is provided by either of the two heretofore known syntheses.

SUMMARY OF THE INVENTION

Briefly, the present invention comprises an improved, azide-based synthesis of tetraamido-macrocyclic ligands as exemplified by 5,6-Benzo-3,8,11,13-tetraoxo-2,2,9,9-tetramethyl-12,12-diethyl-1,4,7,10-tetraazacyclotridecane, $H_4$ in which the synthesis is made very amenable to commercial production and in which the overall yield of the macrocycle is remarkably increased from 12% (Collins et al.) to approximately 50–60% starting from 1,2-phenylenediamine. The improvement in methodology and yield results primarily from the modification of two steps in the synthesis compared to the method of the prior art as follows:

First, the 1,2-phenylenediamine starting material and 2-bromoisobutyryl bromide are reacted in tetrahydrofuran (THF) as opposed to the methylene chloride used in the prior art. The use of THF as solvent is an important improvement over the prior art synthesis because the intermediate reaction product, 1,2-bis(2-bromo-2-methylpropan-amido)benzene, is caused to precipitate directly out of the reaction mixture. The product then only requires filtration for its isolation, thus allowing a much more practical, and commercially very viable method of separation and purification to be used. The method of Collins et al., by contrast, requires that the reaction mixture be extracted multiple sequential times with aqueous hydrobromic acid and aqueous sodium carbonate, a process which is very impractical for large scale synthesis. Additionally, the use of THF as solvent results in a product of increased purity compared to the method reported by Collins et al. (in addition to a small improvement in yield). The increase in purity may further facilitate an increase in yields for the subsequent steps.

Second, in the final cyclization step, in which diethylmalonyl dichloride is reacted with 1,2-bis(2-amino-2-methylpropanamido)benzene to form the macrocycle, this reaction is carried out in (refluxing) ethyl acetate as the solvent as opposed to the methylene chloride used in the prior art. This again allows for a much simplified method of isolation of the macrocycle reaction product because pure product is caused to precipitate out as the reaction progresses. The method also reduces the required addition time of the reactants from many hours to thirty minutes or less. Moreover, the reaction conditions employing ethyl acetate remarkably increase the yield of the macrocycle from about 24%, as obtained for this one step in the prior art, to approximately 60–70% with the method of the present invention. It may be that this surprising increase in yield is effected at least in part by the driving force afforded by the precipitation of the product according to Le Chatelier's principle. It may also be that the formed product is less subject to unwanted side reactions once precipitated. It may further be that use of a higher temperature (i.e., refluxing ethyl acetate versus room temperature methylene chloride) in combination with ethyl acetate as solvent results in a more favorable reaction pathway. In any event, no other solvent investigated afforded this multifold increase in yield and ease of isolation of the product.

The combination of the two improved steps as described above results in the approximately four- to fivefold improvement in overall yield over the method of the prior art and provides, for the first time, a commercially viable synthesis of macrocyclic ligands as denoted by structure 10 in FIG. 1.

DETAILED DESCRIPTION OF THE INVENTION

Figure 1:
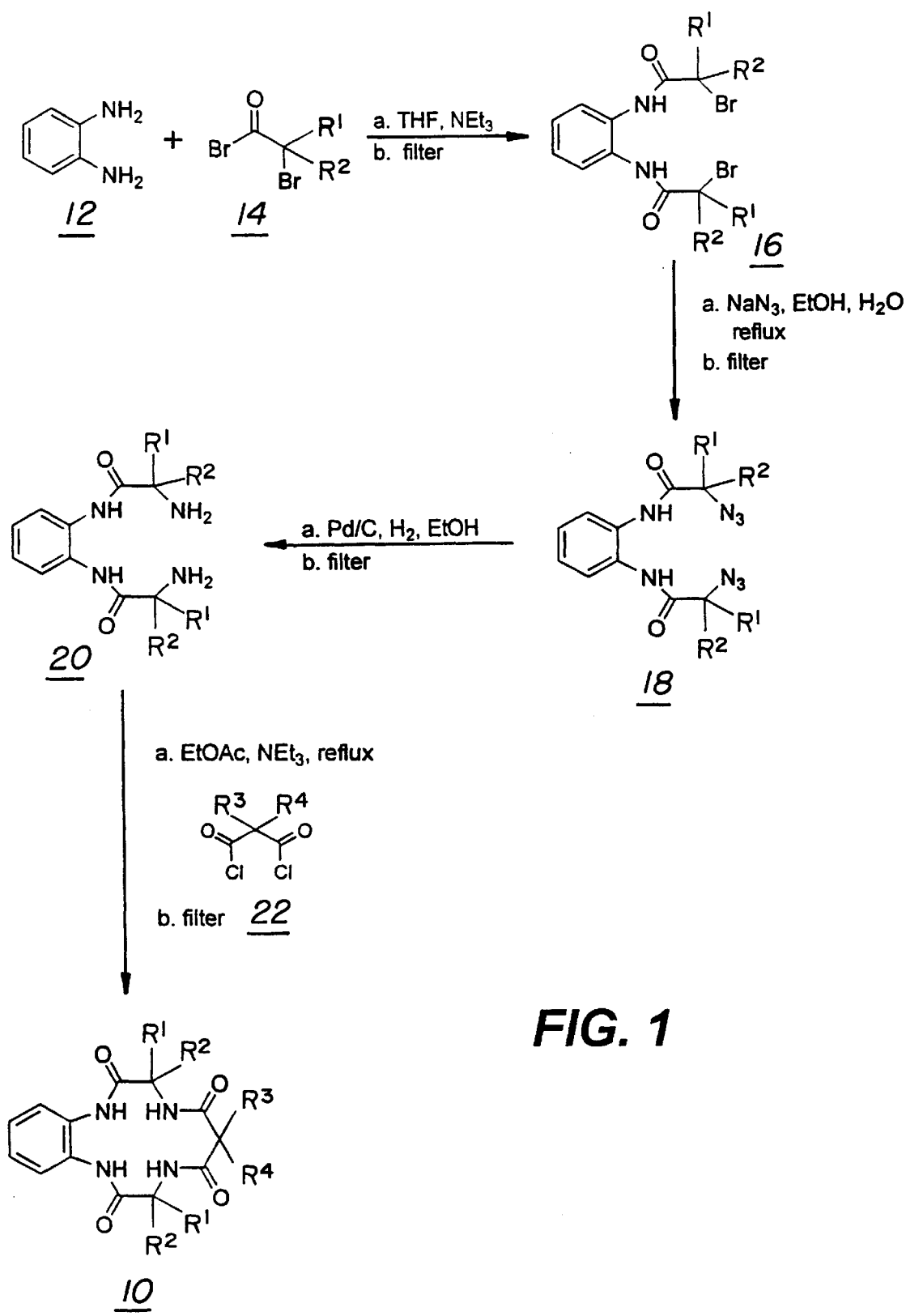
FIG. 1 is a flowchart illustrating the improved synthesis of the tetraamido macrocycle and its precursors according to the present invention.

FIG. 1 illustrates a reaction sequence using industrial-compatible isolation processes for preparing the tetraamido macrocycle 10 in higher yields than was previously possible on any scale. In the preferred reaction sequence, 1,2-phenylenediamine (phenylenediamine 12) and triethylamine are dissolved in anhydrous THF. 2-Bromoisobutyryl bromide (14) ($R^1=R^2$=methyl) is dissolved separately in THF and added dropwise to a solution of the phenylenediamine 12 at room temperature. After addition is complete, the mixture is stirred at room temperature overnight. Preferably, the mixture should be stirred for at least six hours. The mixture is then filtered to remove the crude product, 1,2-bis(2-bromo-2-methylpropanamido)benzene (dibromide 16) plus triethylamine hydrobromide. The filtered material is washed with an aqueous solution (preferably pure water) to remove the triethylamine hydrobromide from the crude dibromide 16. If further purification is desired, crude dibromide 16 can be recrystallized from ethanol to give the purified dibromide 16 in 95% yield. The isolation and purification techniques are well-suited for the large scale production of dibromide 16 in order to prepare macrocycle 10 in commercially relevant amounts. The use of THF as solvent, from which the dibromide 16 precipitates in a substantially pure form (after simple washing), allows filtration to be used for isolation, which is commercially very favored. Also, the THF can be distilled and recycled. As noted previously, the relatively pure condition of the product also likely enhances the yields of the remaining steps.

In the next step of the improved reaction sequence, the dibromide 16 from the previous step is dissolved in hot ethanol and brought to reflux. An aqueous solution of sodium azide is then added dropwise to the refluxing ethanol solution. The reaction is allowed to proceed at reflux for at least six hours, and preferably for 16 hours, and is then cooled to room temperature. The progress of this reaction is easily monitored, e.g., by thin layer chromatography. The solution is reduced in volume by about 80% by evaporation (e.g., on a rotary evaporator) and additional water is added to help precipitate the product, 1,2-bis(2-azido-2-methylpropanamido)benzene (diazide 18). The mixture is cooled and filtered to isolate diazide 18 as a water-wet solid, which is then washed well with water to remove any remaining sodium azide. This very industry favorable procedure for isolating the azido-intermediate by forced precipitation with water and filtration results in a very pure product and eliminates the need to perform the methylene chloride extractions reported in the procedure of Collins et al. In addition, the method of precipitating the diazide 18 with water also contributes to the increase in yield.

Wet diazide 18 is then dissolved in ethanol and hydrogenated using palladium on charcoal as the catalyst. The reaction is monitored by IR spectroscopy to verify complete reduction of the azido groups. After hydrogenation is complete, the catalyst is filtered off and the filtrate is dried on a rotary evaporator and under high vacuum to give 1,2-bis(2-amino-2-methylpropanamido)benzene (diamine 20) in 100% crude yield (95% purity by NMR=95% yield) from dibromide 16. This product may be used as is, or may be purified by recrystallization from isopropyl alcohol to obtain an analytical sample. In contrast, Collins et al. report a 57% yield for the comparable sequence of the two steps of azide formation and hydrogenation for their synthesis. As indicated earlier, the substantial increase in yield for this two step sequence may be due to the relatively high purity of the dibromide 16 used, which is a direct result of the use of THF as a precipitate-forcing solvent during formation of the dibromide 16. It will be apparent to those with ordinary skill in the art that methods other than hydrogenation with a platinum group metal, e.g., reduction with ammonium sulfide, might be employed for reduction of the azido groups.

Diamine 20 prepared in the previous step is dissolved in an organic solvent which is preferably a mixture of methylene chloride and ethyl acetate. The minimum amount of methylene chloride is used to maintain the diamine 20 in solution. Diethylmalonyl dichloride (dichloride 22) ($R^3=R^4$=ethyl) is dissolved separately in ethyl acetate. Both solutions are pumped simultaneously into a large reaction vessel containing refluxing ethyl acetate and triethylamine (2–3 molar equivalents). The triethylamine acts to scavenge the hydrogen chloride generated in the reaction. Other tertiary amino hydrogen chloride scavengers can be substituted for the triethylamine.

The addition of the two solutions into the reaction vessel is done over a time period of about 20–30 minutes. After the addition is complete, the reaction mixture is refluxed for another eight hours and then reduced in volume by distilling off some of the solvent. The reaction is allowed to cool and the product 5,6-benzo-3,8,11,13-tetraoxo-2,2,9,9-tetramethyl-12,12-diethyl-1,4,7,10-tetraazacyclotridecane, $H_4$, macrocycle 10, and triethylamine hydrochloride are filtered and washed with a little ethyl acetate. The solid collected by filtration is washed again with water to remove the triethylamine hydrochloride and the remaining solid is dried in a vacuum oven to give the macrocycle 10 in very good purity and in 60–70% yield from diamine 20, versus a yield of 24% obtained by Collins et al.

In addition to the superior yield, the methodology used by the present invention for synthesis of the macrocycle 10 from diamine 20 is also much simpler to perform than that described by Collins et al. In the method of Collins et al., diamine 20 and dichloride 22 are added in four separate portions at three hour intervals and the resulting mixture is then stirred for 12 hours. The reaction solution must then be extracted repeatedly with aqueous solutions of HBr and $Na_2CO_3$ and the final product must be purified by column chromatography in which portions of the eluted column are "sliced" and the sliced portions extracted, a process which is commercially highly unsuitable. The cumbersome process and poor yield of Collins et al. makes the preparation of commercially useful quantities of the macrocycle 10 very burdensome. In contrast, by the use of ethyl acetate as solvent and with the methodology described, the improved synthesis of the present invention provides that the addition of reactants is completed in twenty to thirty minutes, that the product macrocycle 10 is formed in good yield, and that the macrocycle 10 is caused to precipitate out of solution, thereby allowing its collection by industry favored filtration. Further, the ethyl acetate can be distilled and recycled.

The overall yield of macrocycle 10 starting from phenylenediamine 12 is about 50–60%, which is 4–5 times better than the overall yield of 12% obtained using the synthesis described by Collins et al. Also, the isolation and purification methods of the present invention allow practical production of commercial quantities of the macrocycle 10 for the first time.

It will be apparent to those with ordinary skill in the art that the synthesis which has been described can easily be adapted for the preparation of tetraamido macrocyclic ligands having substituents other than that of the exemplified macrocycle 10. For example, reacting in the first step of the synthesis a 1,2-phenylenediamine having substituents at any or all of the 3-, 4-, 5- and 6-positions of the phenyl ring with a bromoacid bromide (or compound with equivalent acylating and leaving groups) having $R^1$ and/or $R^2$ other than dimethyl can yield, after azide treatment and reduction, any number of what can generically be referred to as 1,2-bis(2-aminoalkanamido)benzenes. Likewise, a malonyl dihalide can be used in the last step in which $R^3$ and/or $R^4$ are other than diethyl. Thus, and referring to FIG. 1 one last time, $R^1$, $R^2$, $R^3$ and $R^4$ may be any of a wide variety of different substituents such as hydrogen, alkyl (including short and long chains), alkenyl, aryl (including benzyl), halo, etc., and the phenyl ring can be substituted with any of a number of substituents such as nitro, methoxy, halo, etc., as are all well known in the art, in order to make a number of differently substituted macrocycles 10.

Therefore, although the present invention has been described in terms of a presently preferred embodiment, it is to be understood that such disclosure is not to be interpreted as limiting. Various alterations and modifications in addition to those just described will no doubt become apparent to those skilled in the art after having read the above disclosure. Accordingly, it is intended that the appended claims be interpreted as covering all alterations and modifications as fall within the true spirit and scope of the invention.

The following three examples illustrate the preferred methods for preparing compounds 16, 20 and 10 according to the present invention:

EXAMPLE 1

Preparation of 1,2-Bis(2-bromo-2-methylpropanamido)benzene (16)

To a large Morton flask is added solid phenylenediamine (27 grams, 0.25 moles), THF (250 mL), and triethylamine (78 mL). To an addition flask is added 2-bromoisobutyryl bromide (70 mL, 0.57 moles) and THF (55 mL). The acid bromide solution is then added dropwise to the phenylenediamine solution over a period of about 2 hours. The resulting mixture is stirred overnight at room temperature. The resulting solid suspension is filtered and washed with THF. The collected solid is washed with water to remove any triethylamine salts and the remaining solid is dried in a vacuum oven to give 107 grams (107% yield) of "semi-crude" product. This material is recrystallized from ethanol to give 94 grams (94% yield) of essentially product, as determined by $^{13}$C-NMR spectroscopy.

EXAMPLE 2

Preparation of 1,2-Bis(2-amino-2-methylpropanamido)benzene (20)

To a large round-bottom flask is placed 1,2-Bis(2-bromo-2-methylpropanamido)benzene (92.9 grams, 0.228 moles). Absolute ethanol (1.2 L) is added and the resulting solution is heated under reflux. A solution of sodium azide (33.9 grams, 0.521 moles) in water (100 mL) is added dropwise via an addition funnel and the resulting homogeneous solution is refluxed overnight. The reaction mixture is cooled to room temperature and reduced in volume about 80% on a rotary evaporator. Cold water is added to the reaction mixture and, upon further stirring, crude 1,2-bis(2-azido-2-methylpropanamido)benzene precipitates as a white solid. The crude diazide is isolated as the water-wet solid by filtration and washing with water. The diazide is then dissolved in warm ethanol (800 mL) and hydrogenated using 5% palladium-on-carbon catalyst until the azido peak is no longer detected by IR. The resulting solution is filtered to remove the catalyst and evaporated to dryness on a rotary evaporator to yield the desired product as a pale-yellow solid (63.8 grams, 100% yield). The product is pure enough to be used as-is, or can be recrystallized from isopropyl alcohol to obtain an analytical sample.

EXAMPLE 3

Preparation of 5,6-Benzo-3,8,11,13-tetraoxo-2,2,9,9-tetramethyl-12,12-diethyl-1,4.7,10-tetraazacyclotridecane, $H_1$ (10)

A 1 L three-neck round-bottom flask was equipped with a reflux condenser and two 250 mL addition funnels. 1,2-Bis(2-amino-2-methylpropanamido)benzene (10 g, 35.9 mmol) was dissolved in a methylene chloride/ethyl acetate solution (5:1, 180 mL) and transferred into one of the addition funnels. Diethylmalonyl dichloride (6.8 mL, 39.5 mmol) was dissolved in ethyl acetate (180 mL) and transferred to the other addition funnel. A stirring solution of ethyl acetate (180 mL) and triethylamine (11 mL, 79 mmol) was brought to reflux. Over a 20 minute period, the solutions in the two addition funnels were added simultaneously to the refluxing reaction, resulting in a cloudy white, heterogeneous mixture. After the additions were complete, the reaction was allowed to reflux an additional 8 hours. The solvents were then concentrated in vacuo and the remaining white solid was transferred to a vacuum filter. The crude solid was washed with ethyl acetate (15 mL) and water (50 mL). The resulting white solid was dried in a vacuum oven (10.2 g, 71%) and was pure by NMR analysis.

What is claimed is:

1. A method for synthesizing a tetraamido-macrocycle comprising:

dissolving a quantity of a 1,2-bis(2-aminoalkanamido)benzene in ethyl acetate sufficient to yield a first reaction solution;

dissolving a quantity of a malonyl dihalide in an ethyl acetate solution sufficient to yield a second reaction solution;

adding the first reaction solution and the second reaction solution to a reaction vessel containing a third reaction solution comprised of ethyl acetate and an acid scavenger to form a reaction mixture; and isolating a solid product comprised of a tetraamido-macrocycle from the reaction mixture.

2. The method of claim 1 wherein the third reaction solution is at reflux during the addition.

3. The method of claim 1 wherein the dissolving step further includes methylene chloride.

4. The method of claim 1 wherein the acid scavenger is triethylamine.

5. The method of claim 1 wherein the first reaction solution and the second reaction solution are added to the reaction vessel simultaneously over a period of about thirty minutes or less.

6. The method of claim 1 wherein the step of isolating the solid product comprises the step of filtering the reaction mixture to yield a crude solid product.

7. The method of claim 1 further comprising the step of washing the crude solid product with an aqueous solution.

8. The method of claim 1 wherein the 1,2-bis(2-aminoalkanamido)benzene is 1,2-bis(2-amino-2-methylpropanamido)benzene.

9. The method of claim 1 wherein the malonyl dihalide is diethylmalonyl dichloride.

10. A method for synthesizing a tetraamido-macrocycle comprising:

forming a first solution comprised of a quantity of a 1,2-phenylenediamine, an acid scavenger and tetrahydrofuran;

adding a volume of a bromoacid bromide to the first solution to yield a first reaction mixture;

isolating a first solid product comprised of a 1,2-bis(2-bromoalkanamido)benzene from the first reaction mixture by filtration;

converting the first solid product to a second solid product comprised of a 1,2-bis(2-aminoalkanamido)benzene;

dissolving the second solid product in ethyl acetate to yield a first reaction solution;

dissolving a quantity of a malonyl dihalide in an ethyl acetate solution to yield a second reaction solution;

adding the first reaction solution and the second reaction solution to a reaction vessel containing a third reaction solution comprised of ethyl acetate and an acid scavenger to form a second reaction mixture; and isolating a third solid product comprised of a tetraamido-macrocycle from the second reaction mixture.

11. The method of claim 10 wherein the third reaction solution is at reflux during the addition.

12. The method of claim 10 wherein the acid scavenger is triethylamine.

13. The method of claim 10 wherein the 1,2-phenylenediamine is unsubstituted.

14. The method of claim 10 wherein the bromoacid bromide is 2-bromoisobutyryl bromide.

15. The method of claim 10 wherein the step of converting the first solid product comprised of a 1,2-bis(2-bromoalkanamido)benzene to the second solid product comprised of a 1,2-bis(2-aminoalkanamido)benzene further comprises:

dissolving the first solid product in ethanol to yield a second solution;

adding an aqueous solution of sodium azide to the second solution to form a reaction mixture;

refluxing the reaction mixture;

cooling the reaction mixture to yield a cooled solution;

reducing the volume of the cooled solution by evaporation;

adding water to the cooled solution to force precipitation of an intermediate solid product comprising a 1,2-bis(2-azidoalkanamido)benzene;

isolating the intermediate solid product by filtration; and reducing the intermediate solid product to yield the second solid product comprising a 1,2-bis(2-aminoalkanamido)benzene.

16. The method of claim 15 wherein the second solution is brought to reflux prior to the addition of the aqueous solution of sodium azide.

17. The method of claim 15 wherein the reduction is performed using hydrogen and palladium on charcoal.

18. A method for synthesizing a tetraamido-macrocycle comprising:

forming a first solution comprised of a quantity of a 1,2-phenylenediamine, an acid scavenger and tetrahydrofuran;

adding a volume of a bromoacid bromide to the first solution to yield a first reaction mixture;

isolating a first solid product comprised of a 1,2-bis(2-bromoalkanamido)benzene from the first reaction mixture by filtration;

dissolving the first solid product in ethanol to yield a second solution; adding an aqueous solution of sodium azide to the second solution to form a second reaction mixture;

refluxing the second reaction mixture;

cooling the second reaction mixture to yield a cooled solution;

reducing the volume of the cooled solution by evaporation;

adding water to the cooled solution to force precipitation of a second solid product comprising a 1,2-bis(2-azidoalkanamido)benzene; isolating the second solid product by filtration;

reducing the second solid product to yield a third solid product comprising a 1,2-bis(2-aminoalkanamido)benzene;

dissolving the third solid product in ethyl acetate to yield a first reaction solution;

dissolving a quantity of a malonyl dihalide in an ethyl acetate solution to yield a second reaction solution;

adding the first reaction solution and the second reaction solution to a reaction vessel containing a third reaction solution comprised of ethyl acetate and an acid scavenger to form a third reaction mixture; and isolating a fourth solid product comprised of a tetraamido-macrocycle from the second reaction mixture.

19. The method of claim 18 wherein the second solution is brought to reflux prior to the addition of the aqueous solution of sodium azide.

20. The method of claim 18 wherein the third reaction solution is at reflux during the addition.

* * * * *